US005773305A

United States Patent [19]
Zabetakis et al.

[11] Patent Number: 5,773,305
[45] Date of Patent: Jun. 30, 1998

[54] SAMPLE DILUTION MODULE

[75] Inventors: George E. Zabetakis, Bethel, Conn.; Paul Gherson, Yorktown Heights, N.Y.

[73] Assignee: Bayer Corp., Tarrytown, N.Y.

[21] Appl. No.: 641,825

[22] Filed: May 2, 1996

[51] Int. Cl.$^6$ .................................. G01N 1/14; B01L 3/02
[52] U.S. Cl. .......................... 436/179; 436/54; 436/174; 436/180; 422/81; 422/100; 73/864.11; 73/864.12; 73/864.22
[58] Field of Search .............................. 422/99, 100, 81; 436/54.1, 174, 179, 180; 73/864.01, 864.11, 864.12, 864.22

[56] References Cited

U.S. PATENT DOCUMENTS

| | | | |
|---|---|---|---|
| 1,547,562 | 7/1925 | Byrd | 422/100 |
| 2,104,325 | 1/1938 | Juffa | 422/100 |
| 2,398,737 | 4/1946 | Elliot et al. | 422/100 |
| 2,595,493 | 5/1952 | Slaby et al. | 73/864.01 |
| 2,697,945 | 12/1954 | Dovas | 422/100 |
| 2,737,812 | 3/1956 | Haak | 73/864.01 |
| 2,836,979 | 6/1958 | Ryley | 422/100 |
| 4,007,639 | 2/1977 | Haeckel | 73/425.4 P |
| 5,000,921 | 3/1991 | Hanaway et al. | 422/100 |
| 5,045,286 | 9/1991 | Kitajima et al. | 422/100 |
| 5,133,218 | 7/1992 | Offenheimer et al. | 73/864.14 |
| 5,159,842 | 11/1992 | Palmer et al. | 73/864.01 |
| 5,183,765 | 2/1993 | Qureshi et al. | 436/180 |
| 5,218,875 | 6/1993 | Volpe et al. | 73/861.01 |

*Primary Examiner*—Long V. Le
*Attorney, Agent, or Firm*—Rodman & Rodman

[57] ABSTRACT

The method of diluting a fluid sample for analysis in a sample analysis system includes the provision of an aspiration probe with two interior sections. The first interior section of the probe has a first diameter and is proximate the aspiration opening of the probe. The second interior section of the probe has a second diameter of greater magnitude than the first diameter and is located distally of the first section. The probe aspirates in consecutive order selected amounts of fluid sample and diluent into the first interior section of the probe. The fluid sample and diluent are mixed in the second interior section of the probe by moving the sample and diluent back and forth in the second interior section a predetermined number of times. The back and forth movement of diluent and fluid sample in the second interior section of the probe provides substantially uniform mixing of the sample and diluent. The use of a Teflon® probe coated with fluorocarbon oil eliminates the risk of cross-contaminating the sources of fluid sample and diluent.

19 Claims, 3 Drawing Sheets

U.S. Patent    Jun. 30, 1998    Sheet 1 of 3    5,773,305
FIG. 1
FIG. 2
FIG. 3
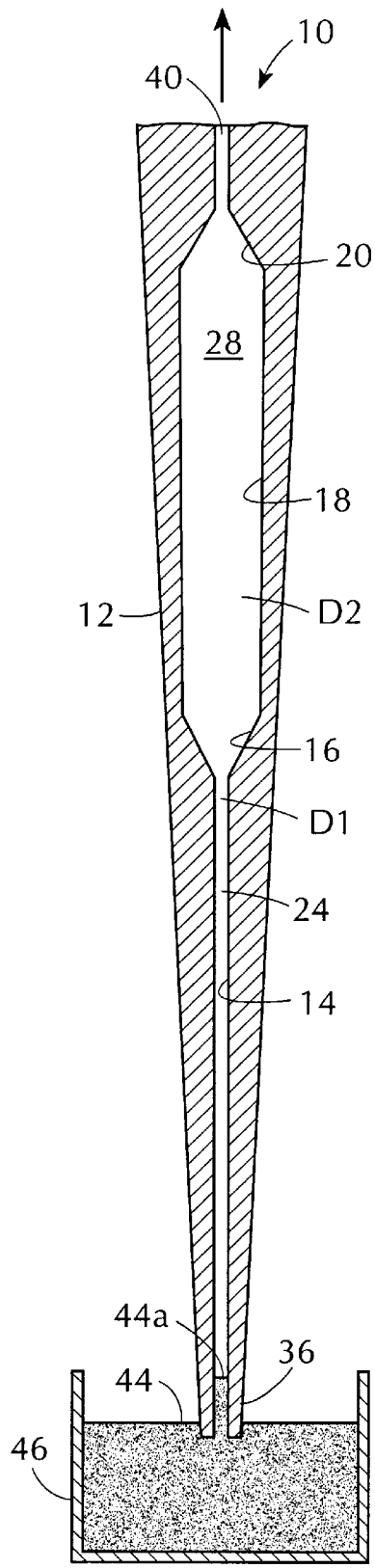
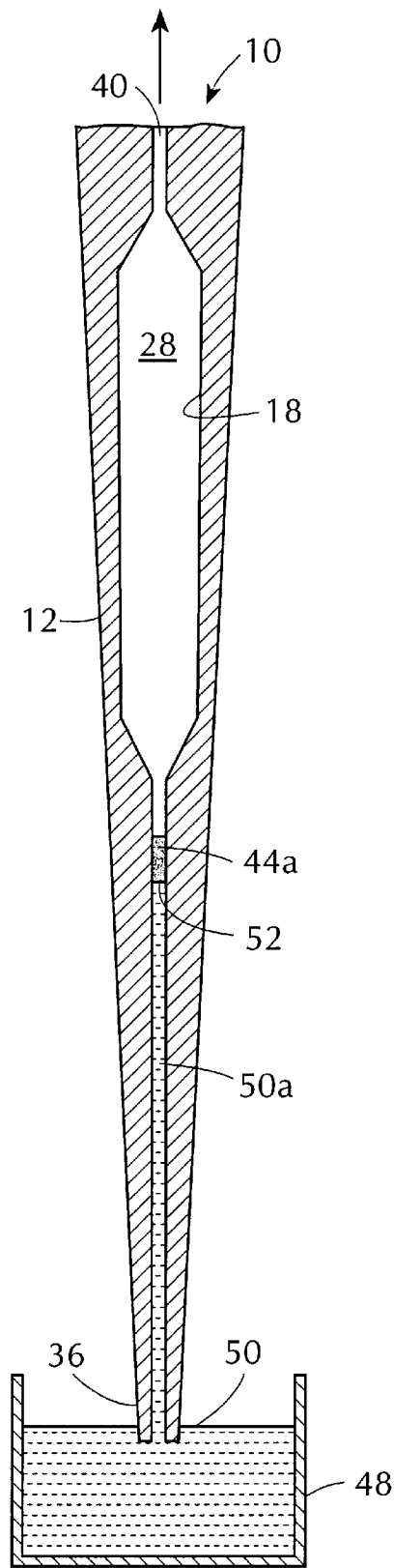
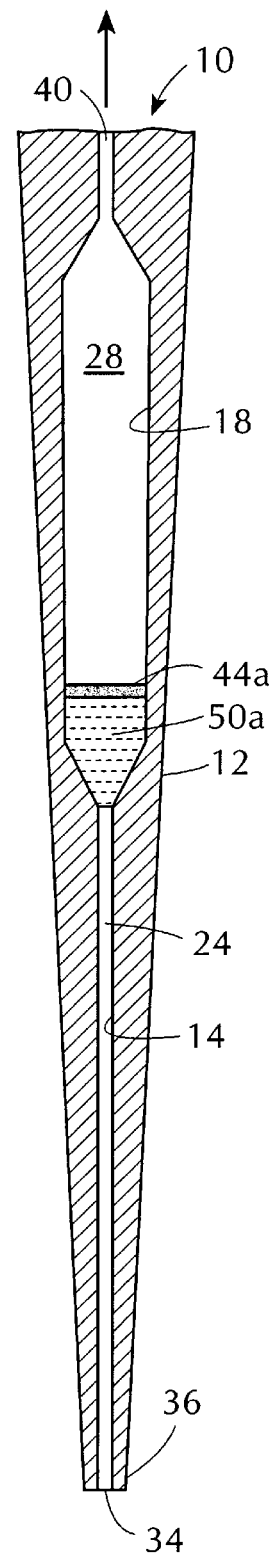

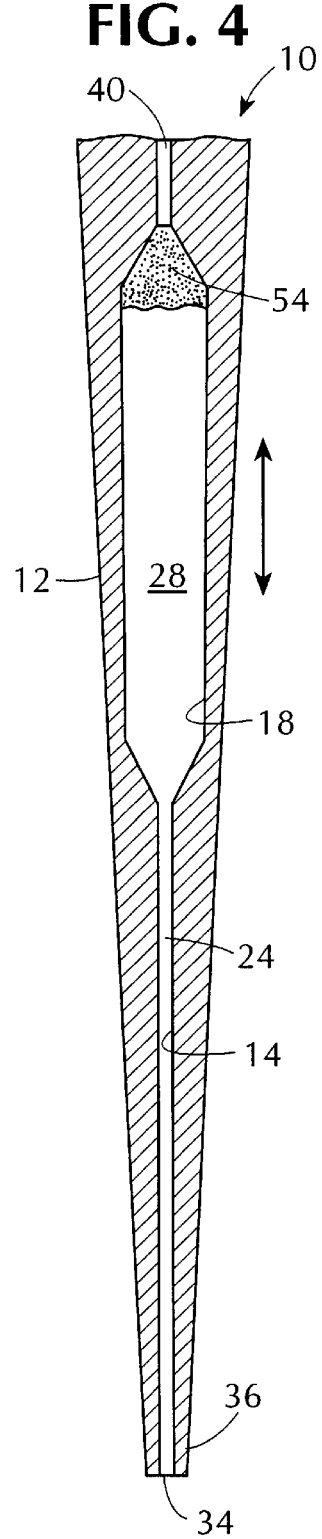
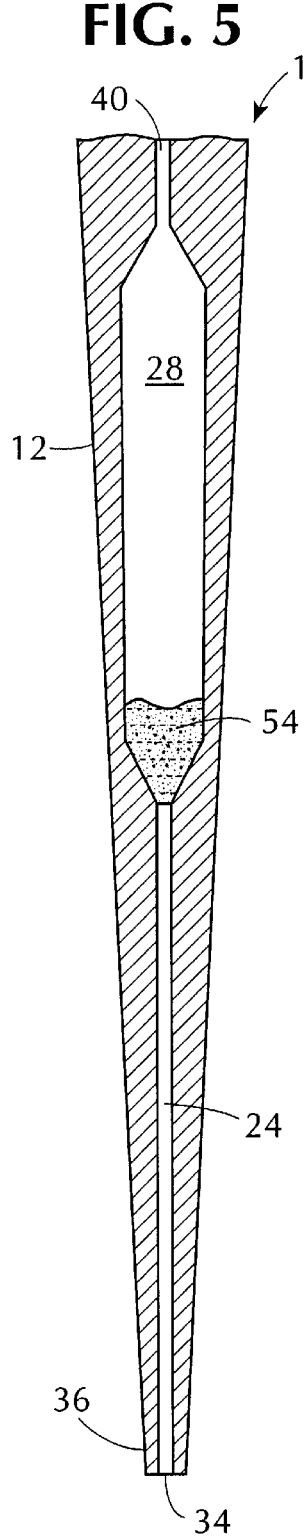
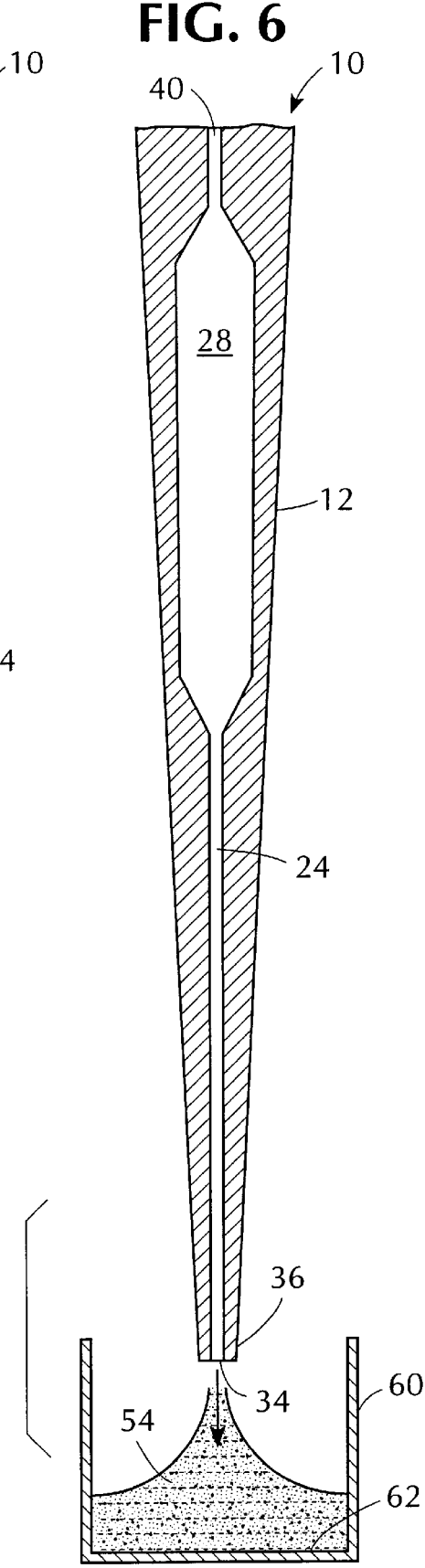

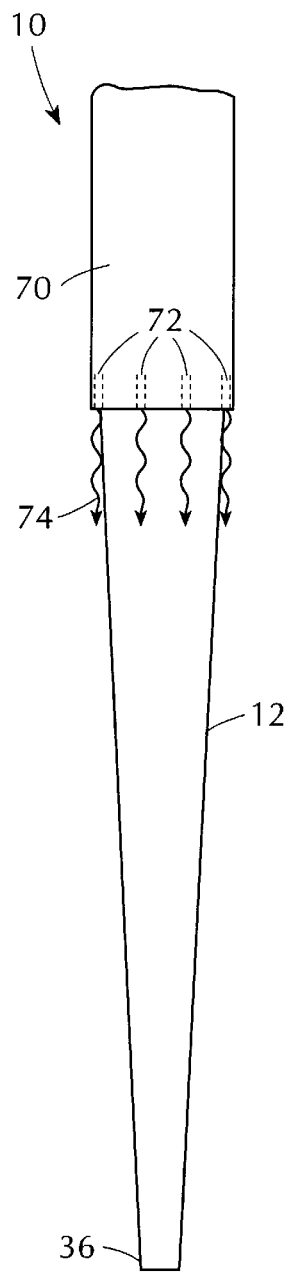
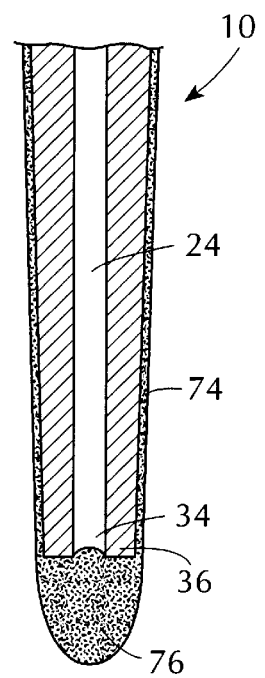
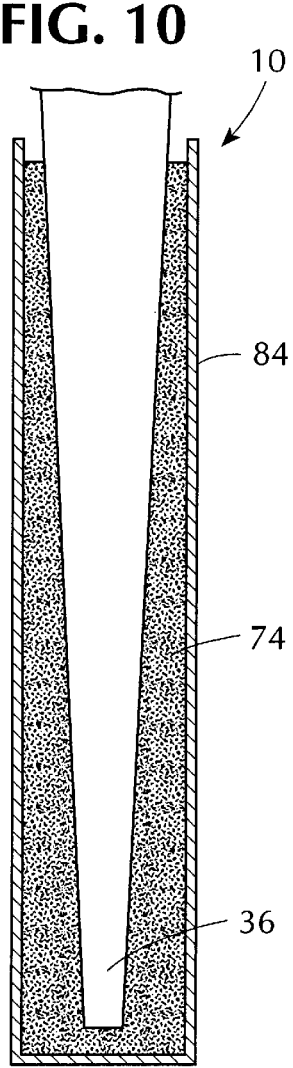
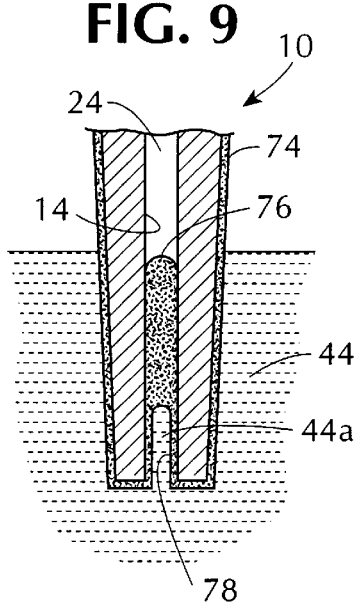
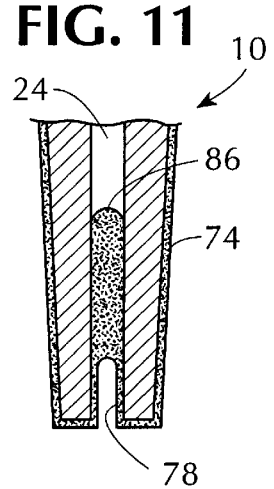

SAMPLE DILUTION MODULE

BACKGROUND OF THE INVENTION

This invention relates to the preparation of fluid samples for automatic analysis in a sample analysis system and more particularly to a novel method of diluting a fluid sample before it is added to a reagent in a sample analysis system.

Automatic testing of a fluid sample in a sample analysis system can provide numerous different tests of the fluid sample at relatively high speed. As shown in U.S. Pat. No. 5,268,147, a plurality of distinctive tests are performed on a fluid sample by first apportioning the fluid sample into a selected number of test packages.

Each apportioned fluid sample is added to a predetermined reagent or combination of reagents to create a specific test reaction or test condition. The results of the test reaction are automatically measured or recorded by components of the sample analysis system.

In many instances, it is desirable to mix and dilute the fluid sample with diluent before the sample is apportioned and added to a reagent. Dilution of the fluid sample helps control a test reaction.

One known method for diluting a fluid sample includes dispensing the fluid sample and the diluent into a mixing container such as a cup or mixing vessel. The fluid sample and the diluent are mixed together by mechanical motion of the container or by stirring the contents of the container to provide a homogeneous diluted fluid sample.

In accordance with the known procedure, the sample and the reagent are dispensed into the mixing container by two separate probes or are sequentially dispensed by a single probe. Subsequently an analyzer probe aspirates a predetermined amount of the homogenized diluted fluid sample, also known as a diluted fluid sample, for transport to a reagent site where the diluted fluid sample is added to a selected reagent or combination of reagents.

One disadvantage of the known procedure described above is that it may require separate probes for dispensing sample and diluent. Another disadvantage is that the probes generally require washing to prevent cross-contamination between sample and diluent. Still another disadvantage is that the mixing container and the stirring or mixing devices can create complexity in a sample analysis system.

It is thus desirable to provide a method for diluting a fluid sample in any desired dilution ratio that does not require separate probes for sample and diluent, does not require washing of the probe and does not require a separate mixing container.

OBJECTS AND SUMMARY OF THE INVENTION

Among the several objects of the invention may be noted the provision of a novel method for diluting a fluid sample, a novel method for diluting a fluid sample wherein a selected amount of fluid sample and a selected amount of diluent are aspirated and mixed together in the aspiration probe, a novel method of diluting a fluid sample which does not require dispensation of the fluid sample into a mixing container for mixing of the diluent with the sample, a novel method of providing different predetermined dilution ratios of fluid sample and diluent mixed together in an aspiration probe, and a novel method of diluting a fluid sample in an aspiration probe.

Other objects and features of the invention will be in part apparent and in part pointed out hereinafter.

In accordance with the invention, the novel method of diluting a fluid sample for analysis in a sample analysis system includes the provision of an aspiration probe with two communicable interior sections having respective inside diameters of different magnitude. A first interior section of the aspiration probe with a first diameter is proximate an inlet opening of the probe, and a second interior section of the aspiration probe with a second diameter of greater magnitude than the first diameter is located distally of the first section with respect to the inlet opening.

A first predetermined amount of fluid sample is aspirated into the first interior section of the aspiration probe, followed by aspiration of a second predetermined amount of diluent into the first interior section of the probe. The fluid sample and diluent are then drawn further into the probe from the first interior section to the second interior section of the probe.

When the fluid sample and diluent are located in the second interior section of the probe, they are moved back and forth in the second interior section a predetermined number of times by alternate vacuum and pressure forces applied to the fluid sample and diluent. Repeated back and forth movement of the fluid sample and diluent a selected number of times in the second interior section of the probe provides substantially uniform mixing of the sample and diluent. The fluid sample and diluent are thus processed into a homogenized mixture within the aspiration probe before being dispensed from the probe.

The present procedure avoids the conventional requirement of a separate mixing container, and a separate stirring or shaking operation outside of the aspiration probe to mix the fluid sample and the diluent.

In accordance with the novel method, a predetermined dilution ratio is established within the probe and the diluted sample as dispensed from the probe has the exact dilution ratio of the initially aspirated separate portions of fluid sample and diluent. More exacting results can thus be achieved in a sample analysis system that applies the present method.

The invention accordingly comprises the method hereinafter described, the scope of the invention being indicated in the claims.

DESCRIPTION OF THE DRAWINGS

In the accompanying drawings,

FIG. 1 is a simplified schematic sectional view of an aspiration and dispensation probe incorporating one embodiment of the invention, the probe being positioned to aspirate a portion of fluid sample from a fluid sample source;

FIG. 2 is a view similar to FIG. 1, wherein the aspiration probe is positioned to aspirate a portion of diluent following aspiration of the portion of fluid sample;

FIG. 3 is a view similar to FIG. 2 wherein the unmixed aspirated fluid sample and diluent are drawn into a mixing section of the probe;

FIG. 4 is a view similar to FIG. 3 showing the aspirated fluid sample and diluent being moved back and forth in the mixing section of the probe;

FIG. 5 is a view similar to FIG. 4 showing the fluid sample and diluent as a homogeneous mixture after repeated movement back and forth in the mixing section of the probe;

FIG. 6 is a view similar to FIG. 5 showing the diluted fluid sample being dispensed into a holding container;

FIG. 7 is a simplified schematic view of the aspiration and dispensation probe with oil coating ports;

FIG. 8 is an enlarged fragmentary sectional view of the tip end of the probe with an oil-coated exterior and a bead of oil at the inlet end of the probe;

FIG. 9 is an enlarged fragmentary sectional view thereof showing the manner in which the bead of oil is driven into the probe during aspiration of a fluid sample such that the movement of oil inside the probe coats the interior surface of the probe;

FIG. 10 shows another method for coating the exterior and interior surfaces of an aspiration probe with oil; and FIG. 11 shows the manner in which the interior surface of the probe is coated with oil during aspiration of oil.

Corresponding reference characters indicate corresponding parts throughout the several views of the drawings.

DETAILED DESCRIPTION OF THE INVENTION

An aspiration and dispensation probe used for diluting a fluid sample is generally indicated by the reference number 10 in FIG. 1.

The probe 10 can be formed of any suitable material, such as stainless steel. Preferably a coating, such as made of Teflon®, is provided on the outside and inside surfaces of the probe, including the outside surface 12 and the inside surfaces 14, 16, 18 and 20.

The inside surface 14 of the probe 10 defines a first interior section 24 of the probe having a first predetermined diameter D1. The inside surface 18 of the probe 10 defines a second interior section 28 of the probe having a second predetermined diameter D2. The diameter D2 is of greater magnitude than the diameter D1.

An inlet and outlet opening 34 of the probe 10 (FIG. 3) is provided at a tip end 36 of the probe for aspiration and dispensation of fluid.

The interior sections 24 and 28 are communicable with each other and with an interior passage 40 that communicates with a known pumping device (not shown). The pumping device provides aspiration suction at the interior sections 28 and 24, when it is desired to aspirate fluid inside the probe 10. The pumping device also provides a pressure force at the interior sections 28 and 24 when it is desired to dispense fluid from the inner sections 24 and 28 of the probe 10.

In carrying out the method of the present invention, a predetermined amount of fluid sample 44 from a fluid sample source 46 is aspirated into the inlet end 34 of the probe 10. The aspirated fluid sample is referred to as a fluid sample segment 44a. The probe 10 is then moved in any suitable known manner to a source 48 of diluent 50 and a predetermined amount of diluent 50 is aspirated into the inner section 24 of the probe 10. The aspirated diluent is referred to as a diluent segment 50a.

Preferably, the first interior section 24 has a length which accommodates the aspirated fluid sample segment 44a and the diluent segment 50a. The aspiration of the fluid sample segment 44a and the diluent segment 50a can be accomplished without any air bubbles between the adjacent segments 44a and 50a of sample and diluent. Since there is contact between the fluid sample segment 44a of the diluent segment 50a at an interface 52 (FIG. 2), some mixing between the two components 44a and 50a can occur as a result of diffusion.

If desired, an air bubble of sufficient size to prevent contact between the fluid sample 44a and the diluent 50 can be aspirated between the sample 44a and the diluent 50a.

The air bubble (not shown) will prevent mixing between the fluid sample 44a and the diluent 50a while they reside in the first interior section 24.

The probe 10 is then moved away from the diluent source 48. The pumping means for the probe 10 draws the fluid sample segment 44a and the diluent segment 50a into the second interior section 28 of the probe, as shown in FIG. 3, for mixing. Mixing of the fluid sample segment 44a and the diluent segment 50a is accomplished by running the combined fluid sample segment 44a and the diluent segment 50a back and forth in the second interior section 28 of the probe 10, as shown schematically in FIG. 4.

Preferably the stroke length for back and forth movement of the combined fluid sample segment 44a and the diluent segment 50a in the second interior section 28 is at least two times the length of the fluid sample segment 44a and the diluent segment 50a in the second interior section 28.

Thorough mixing of the fluid sample segment 44a and the diluent segment 50a can be accomplished by moving the combined fluid sample segment 44a and the diluent segment 50a back and forth in the second interior section 28 approximately five to twenty times.

The resulting homogenized mixture of the fluid sample segment 44a and the diluent segment 50a, generally indicated by the reference number 54, and referred to as the diluted fluid sample, is now ready for dispensation. If desired, the diluted fluid sample 54 can be dispensed into a holding container 60, especially if the sample analysis system requires use of a holding container. Diluted fluid sample would then be aspirated from the holding container.

Thus, the exact amount of fluid sample 44 needed for each test and the exact amount of diluent 50 needed for each test is aspirated into the probe 10, as shown in FIG. 2. Homogenization by mixing of the fluid sample segment 44a and the diluent segment 50a, as shown in FIG. 4, is accomplished each time there is a need for diluted fluid sample 54 to be added to a reagent or reagent combination.

After the sample and diluent have been uniformly mixed in the probe, a reagent can be aspirated along with the sample and diluent. The reagent can be thoroughly mixed with the mixed sample and diluent, in the same manner that the sample and diluent were mixed. Mixing of the reagent with the diluted sample starts a desired reaction of the diluted sample with the reagent. The entire mixture of sample, diluent and reagent can then be dispensed into a cuvette for incubation and completion of the reaction.

If it is necessary to delay start of the reagent reaction with the diluted sample until all components reach the large diameter mixing portion of the probe, a small air bubble can be aspirated before the reagent is aspirated.

In some instances a relatively large dilution ratio of sample to diluent is required. The amount of diluted sample in the probe may then be excessive with regard to the amount desired for a reaction with reagent. Thus the surplus or unneeded portion of the diluted sample can be dispensed from the probe into a waste container, leaving behind in the probe the desired amount of diluted sample needed for reaction. The reagent is then aspirated in the manner previously described to begin a desired reaction within the probe between the precise amount of diluted sample needed and the aspirated reagent.

The dimensions of the first and second interior sections 24 and 28 of the probe can vary, depending upon the particular requirements of the sample analysis system. Nevertheless, to exemplify the magnitudes being dealt with, the first interior section 24 can have a length of 50 mm and an inner diameter D1 of 1 mm. The second interior section 28 can have a length of 50 mm and an inner diameter D2 of 3 mm.

The mixing rate of fluid sample 44a and diluent 50a within the second interior section 28 is approximately one reciprocation per second.

A typical amount of the fluid sample 44 that might be aspirated in the probe 10 is approximately 1 to 20 microliters. An additional volume of the diluent 50 is aspirated to complete a desirable sample plus diluent volume of approximately 100 to 600 microliters.

Thus, if 2 microliters of the fluid sample 44 are aspirated in the probe 10 and a total desired volume of fluid sample plus diluent is 100 microliters, then an additional 98 microliters of the diluent 50 would be aspirated in the probe 10 for mixing purposes.

If 20 microliters of the fluid sample 44 are needed, then an additional 80 microliters of the diluent 50 would be aspirated in the probe 10. In this manner, different dilution ratios between sample and diluent can be aspirated, and thoroughly mixed in the aspiration probe 10 before being dispensed or added to a reagent.

The probe 10 is thus conveniently used to provide different fluid sample dilution ratios for separate different portions of fluid sample, if needed, for a particular reagent or combination of reagents, depending upon test requirements in the sample analysis system.

Because of repeated probing of the fluid sample 44 and the diluent 50 in the containers 46 and 48, it is desirable to prevent contamination of the diluent 50 by the fluid sample 44 or vice versa during aspiration from the containers 46 and 48. The probe 10 is thus coated inside and out with a thin layer of liquid that is immiscible with either the sample 44 or the diluent 50. A suitable immiscible liquid can be fluorocarbon oil.

Referring to FIG. 7, the probe 10 includes a collar portion 70 with oil ports 72 for distributing oil 74 along the outside surface 12 of the probe 10 in a known manner, as shown in FIG. 8. A bead of oil 76 forms at the tip end 36 of the probe 10 when a predetermined amount of oil is permitted to run down the outside surface 12 of the probe 10.

Aspiration of the fluid sample 44 with the bead of oil 76 located at the tip end 36 of the probe 10 causes the fluid sample 44 to drive the bead of oil 76 into the first interior section 24 in a known manner, as shown in FIG. 9. The bead of oil 76 thus coats the inside surface 14 of the first interior section 24 with an oil coating 78 in the known manner shown in FIG. 9. Subsequent aspiration of diluent 50, in the manner shown in FIG. 2, will drive the bead of oil 76 further upwardly into the first interior section 24.

The oil 76 coats a sufficient amount of the inside surface 14 of the probe 10 to ensure that there is no residual adherence of subsequently aspirated ingredients to the probe surfaces and no cross-contamination of the fluid sample 44 and the diluent 50 when such subsequent aspirations of fluid sample 44 and diluent 50 are made by the probe 10.

The probe 10 can also be coated with oil 74 by dipping the probe into an oil reservoir 84 in a known manner, as shown in FIG. 10. A small amount of oil 86 from the oil reservoir 84 is aspirated into the first interior section 24, as shown in FIG. 11.

The oil coating on the inside and outside surfaces of the probe 10 need not be washed off after each mixing cycle.

The known oil coating techniques shown in FIGS. 7–11 are used in connection with the aspiration and mixing cycles shown in FIGS. 1–6, but the oil coatings have been omitted from FIGS. 1–6 for purposes of clarity.

Some advantages of the invention evident from the foregoing description include a novel method of diluting a fluid sample for analysis in a sample analysis system wherein a portion of fluid sample and diluent are accumulated in a probe, mixed in the probe, and dispensed from the probe as a homogenized mixture with a predetermined dilution ratio.

The exact amount of sample and diluent aspirated in the probe and mixed within the probe can be dispensed directly to a reagent container. Thus, the present process eliminates the need for dispensing a previously aspirated sample and diluent into a separate container for mixing and then re-aspirating the mixed fluid sample and diluent for delivery to a reagent container.

A further advantage is that the same probe can be used to provide different dilution ratios between sample and diluent in a homogeneous mixture ready for dispensation. The present method also eliminates the need for providing separate mixing containers for each different diluent ratio between sample and diluent.

The probe 10 thus operates as a sample dilution module for a sample analysis system, and helps eliminate the need for extra containers for mixing and accumulating each different combination of sample and diluent.

The elimination of separate mixing devices in a sample analysis system is a space-saving advantage that permits overall reduction of the size of a sample analysis system.

Another advantage of the present method is that the mixing within a probe of sample and diluent allows precise control of the dispensation volume of mixed sample and diluent. The accuracy of the sample analysis system is thus improved.

A further advantage of the present method is that it provides accurately predictable dilution precision. For example, under conventional sample dilution procedures a given volume of sample is aspirated and then dispensed into a diluent. However, the volume of sample dispensed into the diluent is usually less than the volume that was aspirated because part of a dispensed sample is often left on the tip of the probe. Thus, an anticipated dilution ratio based on the volume of aspirated sample relative to the volume of diluent is not actually achieved because of the difference between the volume of aspirated sample and the volume of dispensed sample. Such volume difference is known as volume error. Volume error is avoided in the present method because the aspirated sample is not separately dispensed but is mixed in the probe with a given volume of diluent. The dilution ratio is thus precisely controlled.

Still another advantage of the present method is that reagent can be mixed in the same probe in which the sample and diluent are mixed. Thus only one probe is needed to mix sample and diluent and reagent and dispense the reacting mixture to a cuvette as desired.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A method of diluting a sample for analysis in a sample analysis system comprising:

a) providing an aspiration probe with two interior sections of different inside diameter, a first interior section with a first diameter being proximate an inlet opening of the probe and a second interior section with a second diameter being located distally of the first section with respect to the inlet opening and being without any mixing element, the second diameter being of greater magnitude than the first diameter, b) aspirating a first predetermined amount of fluid sample into the first interior section of the probe, c) aspirating a second predetermined amount of diluent into the first interior section of the probe, d) drawing the fluid sample and diluent from the first interior section of the probe into the second interior section of the probe, and e) alternately exerting suction and pressure forces on the fluid sample and diluent in the second interior section of the probe to move the fluid sample and diluent back and forth in the second interior section of the probe a first predetermined number of times without agitation of the probe such that the suction and pressure induced back and forth movement of the sample and the diluent in the second interior section of the probe provides substantially uniform mixing of the fluid sample and the diluent in the second interior section of the probe, resulting in a diluted fluid sample.

2. The method of claim 1 wherein the fluid sample and the diluent in the second interior section of the probe are moved back and forth approximately five to twenty times to accomplish mixing of the fluid sample and the diluent.

3. The method of claim 1 wherein the probe is sequentially disposed in a fluid sample container and a diluent container to aspirate the first predetermined amount of fluid sample and the second predetermined amount of diluent.

4. The method of claim 1 wherein the diluted fluid sample from the second interior section of the probe is dispensed from the probe under predetermined test conditions.

5. The method of claim 1 wherein the diluted fluid sample from the second interior section of the probe is dispensed into an empty container and a second aspiration probe aspirates a predetermined amount of mixed fluid sample and diluent from the container for later dispensation.

6. The method of claim 1 wherein approximately one to twenty microliters of fluid sample is aspirated into the first interior section of the probe, followed by aspiration of a selected amount of diluent such that the total fluid sample plus diluent volume is approximately 100 to 600 microliters.

7. The method of claim 1 wherein the fluid sample and the diluent have a predetermined length in the second interior section of the probe and wherein during mixing of the fluid sample and diluent in the second interior section of the probe the combined fluid sample and diluent is moved back and forth a distance of at least twice the predetermined length of the fluid sample and diluent in the second interior section of the probe.

8. The method of claim 1 wherein the aspirated sample and the aspirated diluent in the first interior section of the probe are aspirated in a manner that results in the fluid sample and the diluent being in contact with each other.

9. The method of claim 8 wherein the aspiration of sample and diluent takes place without production of air bubbles between the sample and diluent in the first interior section of the probe.

10. The method of claim 1 wherein the mixing of sample and diluent takes place substantially within the second interior section of the probe.

11. The method of claim 1 wherein the sample and diluent in the first interior section of the probe are displaced entirely into the second interior section of the probe for completion of the mixing step.

12. The method of claim 1 wherein an air bubble of predetermined size is aspirated between the fluid sample and the diluent to prevent mixing of the sample and the diluent in the first interior section of the probe until the aspirated sample and diluent enter the second interior section of the probe.

13. The method of claim 1 wherein a third predetermined amount of a reagent is aspirated into the first interior section of the probe after the fluid sample and diluent have been moved back and forth the predetermined number of times in the second interior section of the probe.

14. The method of claim 1 wherein the reagent is drawn into the second interior section of the probe and moved back and forth a second predetermined number of times to provide substantially uniform mixing of the diluted fluid sample and the reagent.

15. The method of claim 1 wherein a third predetermined amount of reagent is drawn into the first interior section of the probe before the fluid sample and the diluent are drawn into the second interior section of the probe.

16. The method of claim 15 wherein an air bubble of predetermined size is aspirated into the first interior section of the probe between the reagent and the previously aspirated fluid sample and diluent.

17. The method of claim 16 wherein the reagent is drawn into the second interior section of the probe for mixing with the fluid sample and the diluent.

18. The method of claim 1, including further aspirating a third selected amount of reagent before step e.

19. The method of claim 1, including coating the aspiration and dispensation probe with oil prior to aspirating the fluid sample and diluent.

* * * * *